United States Patent
Pentafragas

(10) Patent No.: US 8,037,881 B2
(45) Date of Patent: Oct. 18, 2011

(54) DRY POWDER INHALER

(76) Inventor: Dimitrios Pentafragas, Pikermi (GR)

(*) Notice: Subject to any disclaimer, the term of this patent is extended or adjusted under 35 U.S.C. 154(b) by 607 days.

(21) Appl. No.: 12/295,955

(22) PCT Filed: May 9, 2007

(86) PCT No.: PCT/GR2007/000027
§ 371 (c)(1),
(2), (4) Date: Oct. 3, 2008

(87) PCT Pub. No.: WO2007/129128
PCT Pub. Date: Nov. 15, 2007

(65) Prior Publication Data
US 2010/0154795 A1  Jun. 24, 2010

(30) Foreign Application Priority Data
May 9, 2006  (GR) .............................. 20060100276

(51) Int. Cl.
*A61M 11/00* (2006.01)

(52) U.S. Cl. .......... 128/203.15; 128/203.21; 128/203.12
(58) Field of Classification Search ............. 128/200.14, 128/203.21, 203.12, 203.15; 604/58
See application file for complete search history.

(56) References Cited

U.S. PATENT DOCUMENTS

| 5,860,419 A | 1/1999 | Davies et al. |
| 7,950,389 B2 * | 5/2011 | Eason et al. ............. 128/203.12 |

FOREIGN PATENT DOCUMENTS

| WO | 94/06497 | 3/1994 |
| WO | 03/082389 | 10/2003 |

* cited by examiner

*Primary Examiner* — Steven Douglas
(74) *Attorney, Agent, or Firm* — Ladas & Parry LLP

(57) ABSTRACT

The present invention relates to an improvement of the mouthpiece of a dry powder inhalation device wherein the medicament is packed in the blisters of single dose blister strips. According to the invention a portion of the air which enters the mouthpiece does not pass through the powder containing blister, but follows an alternative path through the mouthpiece, enabling therefore the modification of the resistance of the device in a simple and cost effective manner.

8 Claims, 3 Drawing Sheets

DRY POWDER INHALER

TECHNICAL FIELD

The present invention refers to a device for the inhalation of medicaments in the form of dry powder wherein the medicament is packed in the blisters of single dose blister strips.

TECHNICAL BACKGROUND

The administration of medicaments by inhalation is one of the most promising approaches in therapy that can be applied to a wide variety of diseases. The first inhaled medicaments were used for the treatment of diseases affecting the airways; however there has been an increased interest recently for the development of inhaled forms of medicaments that target various other diseases, such as diabetes.

The administration of medicaments by inhalation is carried out by using inhalation devices (inhalers). A large number of such devices are comprised in the state of the art. A large category of inhalers includes those wherein the medicament is situated in a receptacle in the form of dry powder and wherein the patient, by using the power of his/hers lungs, creates a streaming of air which carries along the powder which is subsequently inhaled through a mouthpiece. These devices are known as dry powder inhalers (DPIs). The powder in said devices is either situated in a container from where the required amount is measured using an internal mechanism, or it is packed as individual doses in the corresponding receptacles such as blister packs or capsules. The powder comprises the active ingredient which in most cases is combined with one or more excipients.

International patent application WO03082389 discloses a dry powder inhaler wherein the medicament is stored in the blisters of specially designed single dose blister strips. The device comprises a mouthpiece, a blister strip support surface and a strip storage compartment. The strip support surface comprises an attachment point (e.g. a protrusion), a cavity which receives the blister of the strip and guides for the correct alignment and firm placement of the strip. The mouthpiece is movably joined to the support surface in such a way that when the blister strip is placed on the support surface and the mouthpiece is in its basic position, the base of the mouthpiece touches the strip and covers completely the powder containing blister.

The mouthpiece of said device is comprised of three parts, an exterior part and two interior parts of conical shape. The first of the interior parts, whose lower side has two openings and touches the blister of the strip, is divided into two chambers through which the air which enters the mouthpiece carries the powder. Then, the mixture of air and powder passes through the second interior part of the mouthpiece and exits the device.

Although the mouthpiece of the above mentioned device functions satisfactorily, there are some points which could be improved. First, due to the design of the mouthpiece, the resistance of the device is pretty high. The resistance of the device corresponds to the force with which the patient has to inhale in order to receive the medicament. It is desirable that the resistance of the device is not very high, so that the device may be used by a wide variety of patients. Furthermore, when the above device is used, a small amount of powder is accumulated in the interior wall of the mouthpiece. Although the amount powder is so small that the therapeutic efficacy of the device is not affected, this accumulation may create problems after long use since in such cases the device would have to be cleaned.

The present invention solves the above-mentioned problems since on the one hand it provides the possibility of reducing the resistance of the device, and on the other it eliminates the possibility of powder accumulation in the interior of the mouthpiece.

DESCRIPTION OF THE INVENTION

The present invention provides a mouthpiece suitable for use with the device disclosed in the international application WO03082389. The base of the mouthpiece according to the invention is placed immediately above the powder containing blister of the strip and touches it. The dimensions of the base of the mouthpiece are such that it covers completely the powder containing blister.

The mouthpiece comprises three main parts, the first being the external part, i.e. the one that the patient places in his mouth during the inhalation, and the other two being internal parts which are fixed on top of each other. The upper part is generally of conical shape and its top constitutes the exit of the mouthpiece while its base is fixed at the top of the lower part. Said lower part comprises at least one opening for the entrance of the inhaled air into it and two more openings at its base, which also represents the base of the mouthpiece that touches the powder containing blister. The first of the two openings represents the entrance of the air into the blister and the second the exit of the powder from the blister. According to the present invention the exit of the powder from the blister is also the base of a cylinder, which is positioned in a generally vertical orientation with regard to the base of the mouthpiece, the height of said cylinder being at least equal to the height of the lower part of the mouthpiece. The height of the cylinder depends on the properties of each powder and his top may reach the exit of the mouthpiece. It is generally preferred that the height of the cylinder is such that its top does not exceed 50% of the height of the upper part of the mouthpiece. It is particularly preferred that the top of each cylinder does not exceed 20% of the height of the upper part of the mouthpiece, and it is even more particularly preferred that it does not exceed 10% of said height. The top of the lower part of the mouthpiece is sealed by a cover which bears an opening through which the cylinder passes. According to the present invention the size of the opening is larger than the diameter of the cylinder. The gap between the opening of the cover and the cylinder allows for a portion of the air which enters the lower part of the mouthpiece instead of heading towards the powder containing blister, to pass through said gap and to exit the mouthpiece through its upper part. The size of the gap depends on the properties of each powder and on the group of patients that uses the device. It is generally preferred that the overall surface of the gap should be up to three times greater than the surface of the opening(s) for the entrance of the air into the lower part of the mouthpiece. It is more preferred that the surface of the gap should be up to two times greater than the surface of the air opening(s), and it is particularly preferred that it should be up to one and a half times greater than the surface of the air opening(s) for the entrance of the air into the lower part of the mouthpiece.

The mouthpiece disclosed herein has considerable advantages compared to the one disclosed in WO03082389. As it was earlier mentioned, in the mouthpiece of WO03082389 the entire quantity of the air that enters the mouthpiece passes through the two openings at its base, which results in a relatively high resistance of the device. In the present invention the existence of the gap between the opening of the cover of the lower part of the mouthpiece and the cylinder reduces the resistance of the device, since part of the pressure that is created in the air that enters the lower part of the mouthpiece is released when a portion of the air passes through said gap.

Hence the airflow, i.e. the amount of air that passes through the device in a unit of time, is increased and therefore the resistance of the device is reduced. Furthermore, the resistance can be easily modified by changing the size of the opening of the cover, while the remaining parts of the mouthpiece remain unchanged, which means that the device of the present invention can be manufactured and modified in a cost effective and simple manner. The resistance of the device may differ depending on the medicament to be administered or the group of patients that uses it. Additionally, the present invention eliminates the possibility of powder accumulation in the inner walls of the mouthpiece.

The mouthpiece of the present invention may be used with the device disclosed in the international application WO03082389. Thus, another aspect of the present invention is a dry powder inhalation device where the powder is packed in the blister of a single dose blister strip, wherein the device comprises a mouthpiece as described above, a strip support surface and a strip storage compartment. The support surface comprises an attachment point, a cavity which receives the blister of the strip and guides for the correct alignment and firm placement of the blister strips. It is preferred that the attachment point is a protrusion. The mouthpiece is movably joined to the strip support surface so as when the device is ready for inhalation the base of the mouthpiece touches the strip and covers completely the powder containing blister.

The single dose blister strip comprises a base sheet and a cover sheet. The base sheet comprises a powder containing blister and an attachment formation. It is preferred that the attachment formation is a hole. The base sheet is sealed in the area around the blister by a cover sheet whose free end, while initially covering the attachment formation, is folded 180 degrees creating therefore a pulling tab which enables the user to expose the powder by pulling away the cover sheet from the base sheet. The active pharmaceutical ingredient packed in the blister of said strip may be used as such or it may be combined with suitable excipients. The term medicament therefore, used throughout the present description and claims, designates either the pharmaceutical ingredient as such or its combination with suitable excipients.

The device of the present invention is used in the following way: The user lifts the mouthpiece from its basic position and places a strip on the support surface in such a way that the attachment formation of the strip is combined with the attachment point of the support surface. The strip is aligned with the help of the guides and the blister enters the cavity of the support surface. Then, the user returns the mouthpiece to its basic position and exposes the powder by pulling away the cover sheet of the strip. At this point the base of the mouthpiece touches the strip while it covers completely the powder containing blister and the device is ready for inhalation. The user then inhales the powder and then, by lifting the mouthpiece from its basic position in order to remove the used blister, he verifies that he has inhaled the entire dose of the medicament.

DETAILED DESCRIPTION OF THE DRAWINGS

Figure 1:
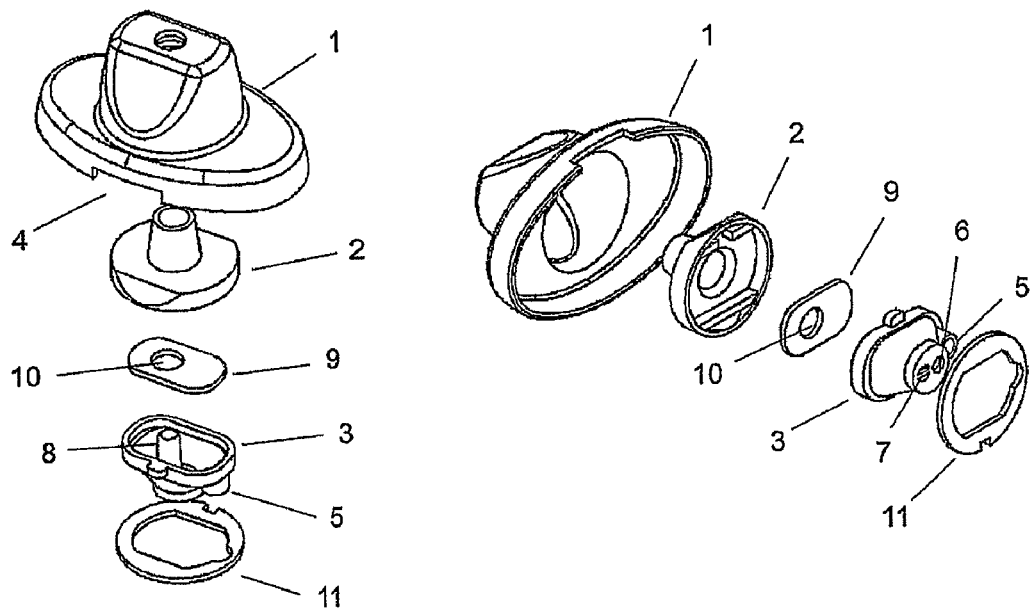
FIG. 1 shows the main parts of the mouthpiece of the present invention.
Figure 2:
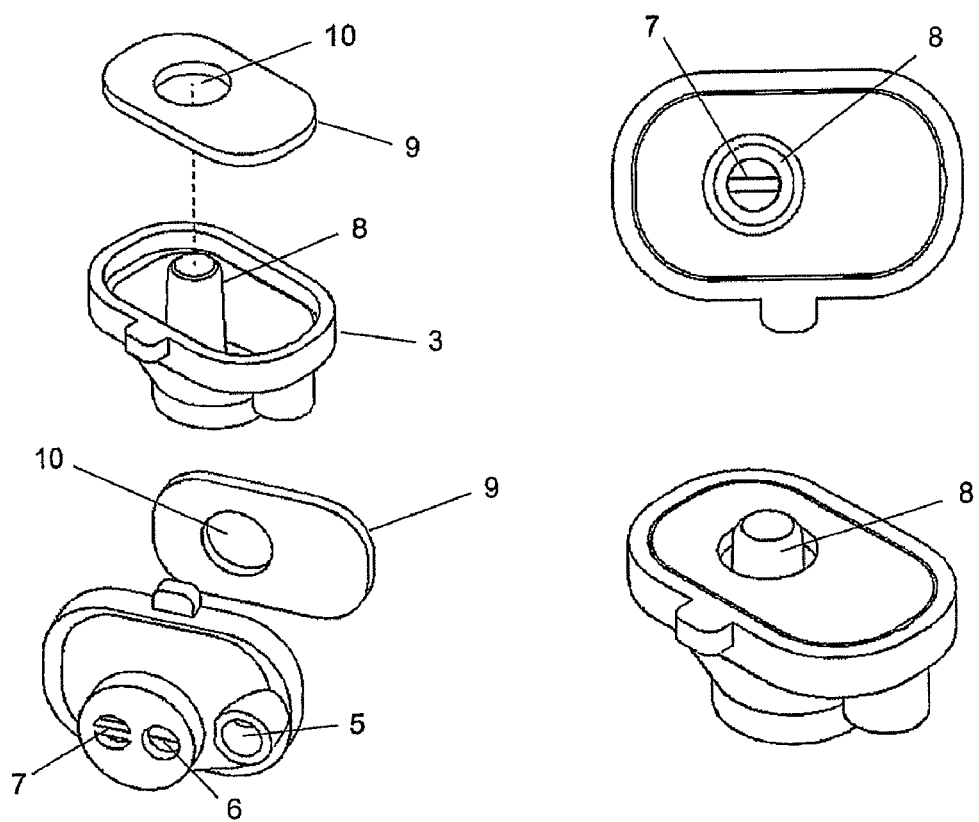
FIG. 2 shows the lower part of the mouthpiece.

FIG. 1 shows an example of the mouthpiece of the present invention. The mouthpiece comprises three main parts: The external part (1), which the patient places in his mouth during the inhalation, and two internal parts which are fixed one on top of the other. In this specific example the base of the external part (1) bears an opening (notch 4) through which the air enters the mouthpiece. The upper internal part of the mouthpiece is a cone (2) which is fixed on the inside of the external part (1). The top of the cone (2) represents the exit of the mouthpiece, while its base is fixed on the top of the lower internal part (3). Said part bears an opening (5) for the entrance of air, and two openings (6) and (7) at its base. The opening (6) represents the entrance of the air in the powder containing blister while the second opening (7) represents the exit of the powder from the blister. As it is shown in FIG. 2 the latter opening (7) is also the base of a cylinder (8) whose height is slightly larger than that of the lower part (3). The top of said part (3) is sealed by a cover (9) which bears an opening (10) through which the cylinder (8) passes. As it is clearly shown in FIG. 2, the size of the opening (10) is larger than the diameter of the cylinder (8) and thus a gap is formed through which a portion of the air that enters the lower part (3) passes, as it is explained herein below. In this specific example the three main parts of the mouthpiece are held together by a ring (11) (FIG. 1).

Figure 3:
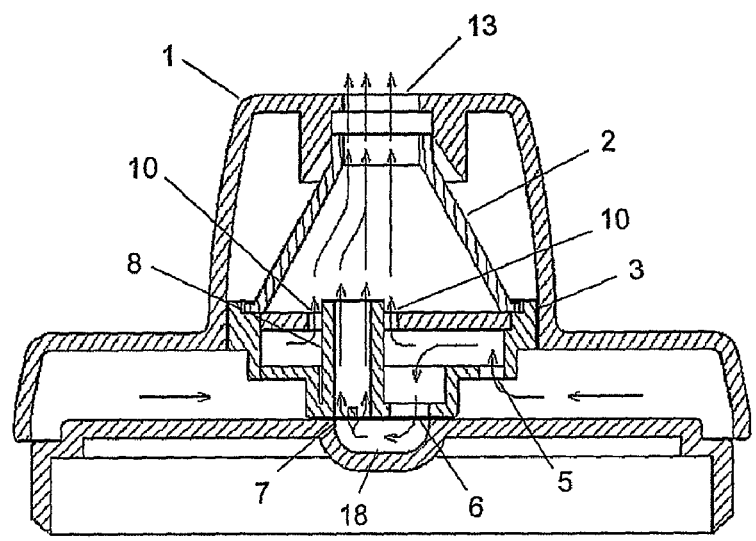
FIG. 3 shows a vertical section of the mouthpiece.

FIG. 3 shows a vertical section of the mouthpiece of the present invention when situated above a powder containing blister, and the airflow through said mouthpiece. The air enters the mouthpiece through one or more openings which are not shown in the drawing. Then through an opening (5) it enters the lower part (3) of the mouthpiece. There, a portion of the air passes through the opening (6) for the entrance of the air into the blister (18), carries along the powder which is contained in the blister (18) of the strip and the mixture of air and powder passes through the opening (7) for the exit of the powder from the blister into the cylinder (8) and from there it enters the upper part (2). A second portion of the air which enters the lower part passes through the opening 10 and enters the upper part 2. This air meets the mixture of powder and air which exits the cylinder (8) and it is combined with them, forming a new mixture of air and powder which exits the mouthpiece through the opening (13).

Figure 4:
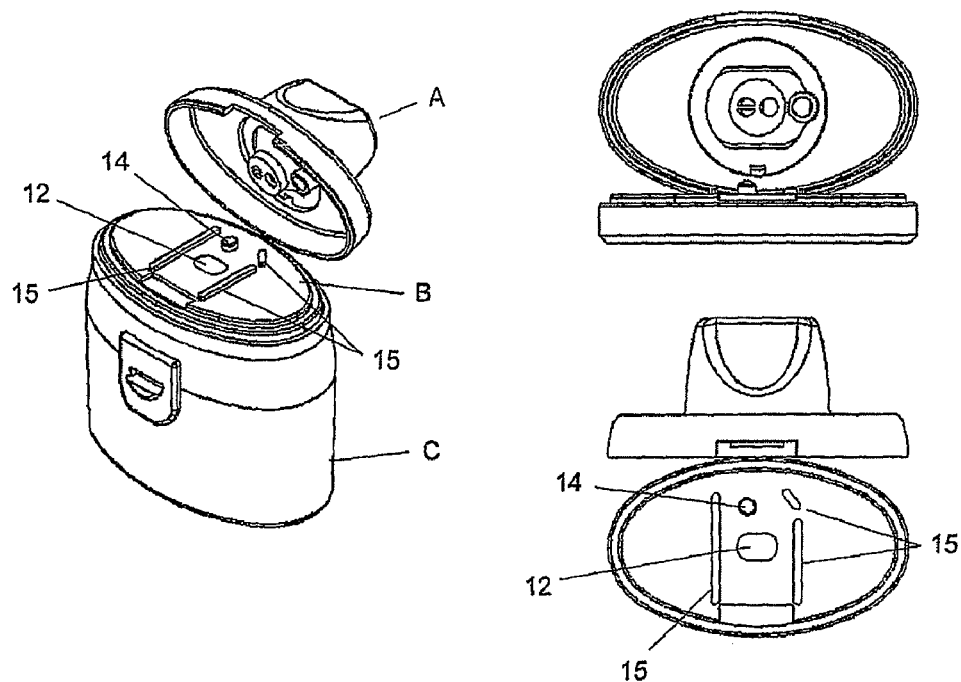
FIG. 4 shows a dry powder inhalation device according to the present invention.
Figure 5:
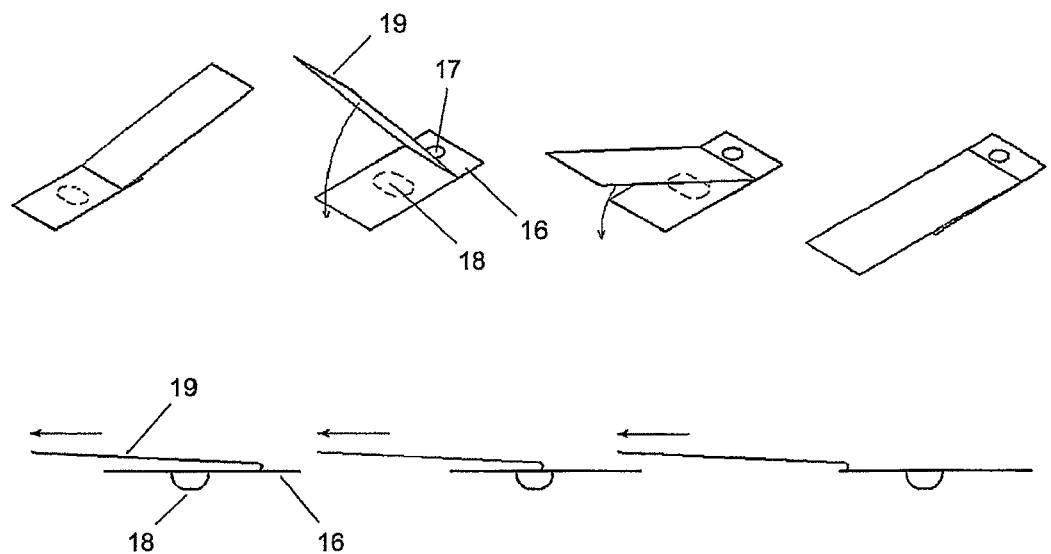
FIG. 5 shows a single dose blister strip.

The mouthpiece of the present invention can be used with the device disclosed in the international application WO03082389 and shown in FIG. 4, where the medicament is packed in the blisters of single dose blister strips (FIG. 5). The device comprises a mouthpiece (A), which is movably joined to the strip support surface (B), said surface comprising an attachment point (in this specific example a protrusion (14)), a cavity (12) which receives the blister of the strip, and guides (15). The device also comprises a strip storage compartment (C).

The single dose blister strip (FIG. 5) comprises a base sheet (16), which comprises an attachment formation (in this specific example a hole (17)) and a powder containing blister (18). The base sheet is sealed in the area around the blister (18) by a cover sheet (19) whose free end while initially covering the hole (17) it is then folded by 180 degrees creating a pulling tab and enabling the user to expose the powder by pulling away the cover sheet (19) from the base sheet (16).

Figure 6:
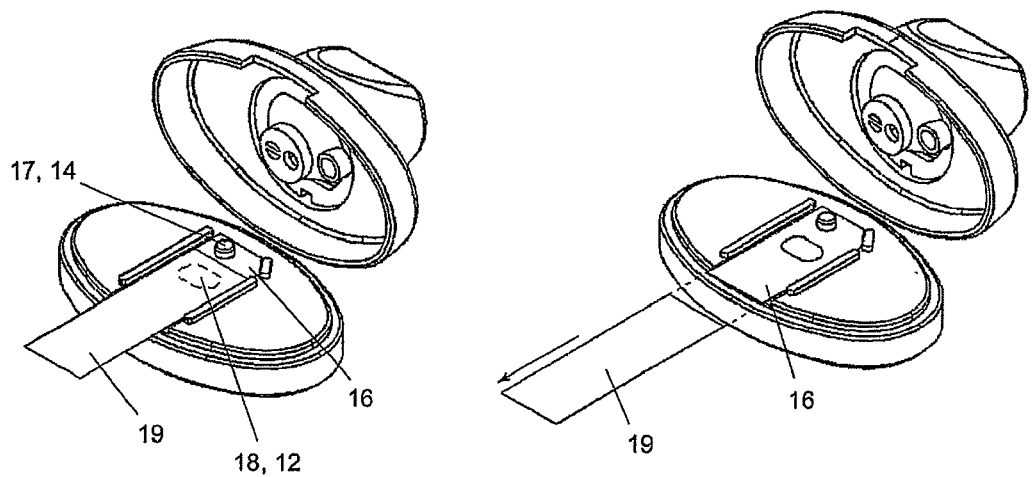
FIG. 6 shows the manner by which the blister strip is placed in the device.

The single dose blister strip is placed in the inhalation device in the way shown in FIG. 6. Thus, the user first lifts the mouthpiece from its basic position and places the strip on the support surface in such a way that the hole (17) of the strip is placed around the protrusion (14) and the blister (18) enters the cavity (12). Then the user returns the mouthpiece to its basic position and pulls the cover sheet (19) until it is detached from the base sheet (16). While keeping the mouthpiece at its basic position the user inhales the powder and then, by lifting the mouthpiece from its basic position in order to replace the used strip, he verifies that he has inhaled the entire dose.

The invention claimed is:

1. An inhalation device for the administration of medicaments in the form of dry powder wherein the medicament is packed in the blisters of single dose blister strips, wherein said device comprises a mouthpiece (A), a strip support surface (B) and a strip storage compartment (C), wherein the mouthpiece (A) is movably joined to the support surface (B), wherein the mouthpiece comprises an upper (2) and a lower (3) internal part, wherein the lower part (3) comprises at least one opening (5) for the entrance of the air into it, an opening (6) for the entrance of the air into the powder containing blister and an opening (7) for the exit of the powder from the blister, wherein the support surface comprises an attachment point (14), a cavity (12) which receives the blister of the strip and guides (15), characterized in that the opening (7) for the exit of the powder from the blister represents the base of a cylinder (8) whose height is at least equal to the height of the lower part (3) of the mouthpiece, and in that the lower part (3) of the mouthpiece is sealed by a cover (9) which bears an opening (10) through which the cylinder (8) passes, and wherein the size of the opening is larger that the diameter of the cylinder (8), leaving a gap between the cylinder (8) and the opening (10).

2. A device according to claim 1, wherein the attachment point is a protrusion (14).

3. A device according to claim 1, wherein the surface of the gap between the opening (10) of the cover (9) and the cylinder (8) is up to three times greater than the surface of all the opening(s) (5) for the entrance of the air into the lower part (3) of the mouthpiece.

4. A device according to claim 3, wherein the surface of the gap is up to two times greater.

5. A device according to claim 4, wherein the surface of the gap is up to one and a half times greater.

6. A device according to claim 1, wherein the height of the cylinder (8) is such that its top does not exceed 50% of the height of the upper part (2) of the mouthpiece.

7. A device according to claim 6, wherein the top of the cylinder (8) does not exceed 20% of the height of the upper part (2) of the mouthpiece.

8. A device according to claim 7, wherein the top of the cylinder (8) does not exceed 10% of the height of the upper part (2) of the mouthpiece.

* * * * *